United States Patent
Weth et al.

[11] Patent Number: 6,068,596
[45] Date of Patent: May 30, 2000

[54] METHOD FOR ADMINISTERING A PULSE-LIKE WAVE TO A PATIENT FOR PAIN THERAPY AND/OR FOR INFLUENCING THE AUTONOMIC NERVOUS SYSTEM

[76] Inventors: Gosbert Weth, Coburger Strasse 6; Gunter Wilhelm, Flinzweg 10, both of D-91056 Erlangen, Germany

[21] Appl. No.: 08/946,721

[22] Filed: Oct. 8, 1997

Related U.S. Application Data

[62] Division of application No. 08/500,950, Aug. 8, 1995, Pat. No. 5,727,556.

[30] Foreign Application Priority Data

Feb. 10, 1993 [DE] Germany ............................. 43 03 830
Dec. 3, 1993 [DE] Germany ............................. 43 41 323

[51] Int. Cl.[7] ........................................................ A61N 7/00
[52] U.S. Cl. .............................. 600/437; 600/472; 601/2; 601/108; 607/46
[58] Field of Search .............................. 607/1–3, 46, 72, 607/73; 601/2, 15, 107, 108; 128/898; 600/437, 439, 9, 14, 10, 472

[56] References Cited

U.S. PATENT DOCUMENTS

| | | |
|---|---|---|
| 3,396,721 | 8/1968 | Mencacci . |
| 3,499,437 | 3/1970 | Balamuth . |
| 3,861,383 | 1/1975 | Kovach . |
| 3,908,634 | 9/1975 | Monaghan . |
| 4,265,228 | 5/1981 | Zoll . |
| 4,324,261 | 4/1982 | Mark et al. . |
| 4,549,535 | 10/1985 | Wing . |
| 4,674,505 | 6/1987 | Pauli et al. . |
| 4,697,588 | 10/1987 | Reichenberger . |
| 4,928,672 | 5/1990 | Grasser et al. . |
| 5,119,832 | 6/1992 | Xavier . |
| 5,131,409 | 7/1992 | Lubarev et al. . |
| 5,160,336 | 11/1992 | Favre . |
| 5,305,731 | 4/1994 | Buchholtz . |

FOREIGN PATENT DOCUMENTS

| | | |
|---|---|---|
| 0 171 423 | 2/1986 | European Pat. Off. . |
| OS 30 38 445 | 5/1982 | Germany . |
| WO 85/03234 | 8/1985 | WIPO . |

OTHER PUBLICATIONS

"Thresholds for Tissue Ablation by Focused Ultrasound," Chapelon et al.,, 1990 Ultrasonics Symposium pp. 1653–1656.

"Abstracts of the 9th International Congress of the International Federation of Manual Medicine," Manuelle Medizin, vol. 27, No. 4, Aug. 1989, p. 8.

Primary Examiner—Kennedy J. Schaetzle
Attorney, Agent, or Firm—Hill & Simpson

[57] ABSTRACT

In an apparatus and a method for pain therapy and/or for influencing the autonomic nervous system, at least one pulse-like wave is conducted onto a neurally sensitive region with an apparatus, namely a source of pulse-like waves the region participating in the conduction with respect to the pain or with respect to the region of the autonomic nervous system to be influenced.

9 Claims, 6 Drawing Sheets

METHOD FOR ADMINISTERING A PULSE-LIKE WAVE TO A PATIENT FOR PAIN THERAPY AND/OR FOR INFLUENCING THE AUTONOMIC NERVOUS SYSTEM

This is a division, of application Ser. No. 08/500,950 filed Aug. 8, 1995, issued as U.S. Pat. No. 5,727,556 on Mar. 17, 1998.

BACKGROUND OF THE INVENTION

1. Field of the Invention

The invention is directed to an apparatus for treating painful conditions and/or for influencing the autonomic nervous system, having a source of pulse-like waves with which at least one pulse-like wave is conducted onto a neurally sensitive region that participates in the conduction with respect to the pain or with respect to the region of the autonomic nervous system to be influenced. The invention is also directed to a method for pain therapy and/or for influencing the autonomic nervous system. The invention is also directed to a new employment of a source of pulse-like waves. As used herein, pain therapy means the alleviation or elimination of the sensation of pain.

2. Description of the Prior Art

In view of the large number of patients that suffer seriously painful conditions, such apparatuses or methods are of great significance since the administration of analgesics has a risk of addiction associated therewith. Moreover, analgesics, particularly given long-lasting administration, represent a considerable stress on the metabolism of the patient. Damage to the metabolic organs, for example the kidneys, can even occur. Moreover, the analgesic must be administered with higher doses with increasing treatment in many instances in order to assure the success of the treatment. Moreover, there are a large number of patients with analgesic incompatibility or allergy. Apparatuses or methods of the type initially cited are likewise of great significance in the treatment of drug addicts during withdrawal in view of the pains and other withdrawal symptoms thereby arising. Finally, apparatuses and methods of the type initially cited are also of significance in view of the large number of patients with autonomic disorders, for example cardiac rhythm disorders, digestion disorders, excessive perspiration, stresses or the like.

Apparatuses or methods of the type initially cited, namely, allow pain therapy and treatment of autonomic disorders entirely without, or at least with diminished, medication.

A method of the type initially cited is known as Atlas therapy and derives from the French physician Arlen (see "Manuelle Medizin", Vol. 27, No. 4, 1989 Edition, page 82, Springer Verlag). In Atlas therapy, the therapy of pains in the spinal column region is enabled by manual pulses (manipulation), particularly striking with fingers onto one of the transverse processes of the first neck vertebra. Moreover, stresses in the spinal column area are positively influenced in durable fashion, i.e. alleviated or entirely eliminated. Even sequela of multiple sclerosis can be improved by Atlas therapy, so that, for example, an acute involution of pareses (paralysis) is possible. It has also been found that autonomic stimuli are also triggered by this therapy, for example that blood circulation is noticeably improved.

It has been biochemically documented that a significant change of the neurotransmitters (for example, dopamine) as well as of the biogenous amines occurs in conjunction with Atlas therapy, this having been documented by biochemical findings in the blood. The change of the neurotransmitters and biogenous amines is thereby not restricted only to the therapy area but may be found in the entire organism.

A disadvantage of Atlas therapy is that it must be manually implemented and, thus, is subject to subjective influences, i.e. cannot be reproduced.

US. Pat. No. 3,499,437 also discloses that a series of pulse-like ultrasound waves be introduced into peripheral regions of the nervous system for pain therapy as well as for influencing the autonomic nervous system. The peripheral regions into which the series of pulse-like ultrasound waves are introduced are regions which participate in nerve signal conduction for the pain to be treated, or for the desire to influence. This is intended to effect a micro massage. A disadvantage of this method is that, due to its peripheral application (similar to stimulation current), it proves successful only after frequent and long-lasting application sessions, if at all.

SUMMARY OF THE INVENTION

It is an object of the present invention to provide an apparatus and a method of the type initially cited but wherein the energy content and temporal curve of the pulse-like wave can be reliably reproduced.

According to the invention, th object relating to the apparatus is achieved in an apparatus for treating painful conditions and/or for influencing the autonomic nervous system having a source of pulse-like waves with which the pulse-like waves are conducted onto a neurally sensitive region which participates in the conduction of the pain or with respect to the region of the autonomic nervous system to be influenced, wherein the chronological spacing between two successive pulse-like waves does not fall below several minutes. The object relating to the method is inventively achieved by a method for pain therapy and/or for influencing the autonomic nervous system, wherein at least one pulse-like wave is conducted with an apparatus onto a neurally sensitive region that participates in the conduction with respect to the pain or with respect to that region of the autonomic nervous system to be influenced. The invention is on the perception that the effectiveness of the Atlas therapy is based because a neurally sensitive region, namely the ganglion cervicale superior, is restimulated by the finger beat, resulting in the readjustment of the nervous pathways dependent on this ganglion, this leading to the elimination or to a reduction of the painful sensations and to a dismantling of the stresses. Compared to manual therapy, the energy content and the chronological curve of the pulse-like wave can be reproduced extremely well in the case of the invention. Moreover, the critical advantage is achieved that significantly higher energies can be supplied to the body of the patient with a single pulse than in the case of manual therapy, so that deep-seated, neurally sensitive regions can also be reached. The term pulse-like wave in the present case means a pulse that essentially involves a one-time pulse-like amplitude modificaton, preferably ensuing from a quiescent condition. As a general rule, moreover, the neurally sensitive region is not identical with the painful region or the region to be influenced, i.e. the painful region or the region to be influenced is not directly charged with the acoustic pressure pulses. This can represent a critical advantage since a possible morbidity in the painful region in the region to be influenced cannot be directly caused by the application of the pressure pulse. It is also critical that a sequence of pulse-like waves is not introduced but only a single pulse-like wave per treatment. A sequence of pulse-like waves would be of little assistance and could even be harmful under certain circumstances because is cannot be assured that the required "restimulation" ensues due to a sequence of pulse-like waves. It is at most conceivable to introduce a second pulse-like wave after several minutes when the first has not led to a noticeable success.

Painful conditions and stresses in the region of the spinal column can be treated well with the invention by charging a neurally sensitive region lying close to a transverse process of the first neck vertebra, for example the ganglion cervicale superior, with the pulse-like wave. A ganglion from the group containing ganglion coeliacum, ganglion cervicale superior, ganglion sacrale and ganglion pelvinum constitutes a neurally sensitive region that is especially well-suited as point of application.

It is assumed that, a "restimulation" of the respective ganglion ensues due to the charging with a pulse-like wave, as a result of which freedom from pain or an influencing of the region of the autonomic nervous system linked to the respective ganglion is achieved.

By contrast to other "manipulations" of peripheral nerve cells, whether with stimulation current, massage or acoustic pulses as well, the present invention applies the pulse-like waves at the centrally regulating control mechanisms of nerve control centers, namely nerve centers and, particularly, ganglia, and rather than engage at peripheral nerve stimulation points lying in the painful region or in the region to be influenced. With the present invention, pain alleviation can be achieved, for example by influencing the ganglion coeliacum, even given pains that are practically resistant to medication therapies. For example, pains caused by a pancreatitis (morbus whipple) or other maladies in the upper abdomen can be overcome. Particularly such pains are nearly always resistant to therapy and require high doses of morphine preparations. Pains in the region of the lumbar vertebra (lumbar spinal column syndrome) and pains in the sacral region can also be well-treated by influencing the ganglion pelvinum.

The pulses conducted onto the ganglia can only achieve their effect when they are adequately short, i.e. lying in the 100 ms (millisecond) range. The pulse duration should preferably not exceed 70 ms.

Additionally, it should be noted that the invention is suitable, for example, for the treatment of the following maladies or in conjunction with the pains occurring in these maladies:

1. painful conditions in rheumatoid conditions and stresses;
2. painful conditions in circulatory disorders (for example, in the legs as a consequence of metabolic disorders or in case of vasospastic conditions, etc.);
3. painful conditions in internal disorders (for example, morbus whipple, angina pectoris, stomach pain, functional upper abdominal complaints, etc);
4. painful conditions in neurological and physiatric illnesses (neuralgia, multiple sclerosis, neuro-vegetative syndrome, stresses, etc.); and
5. painful conditions given tumors and concomitant therapy.

Whereas a one-time charging of the respective ganglion with an acoustic pressure pulse or a pulse-like electromagnetic wave usually produces only a short-duration success, a longer-lasting success (months) wherein the patient can also live without analgesics can be achieved given a multiple, for example three-time repetition of the treatment, for example at week intervals. The repetition of the treatment is not to be confused with the administration of a sequence of pulse-like waves.

It can be expedient under certain circumstances to simultaneously implement a medication therapy with the treatment on the basis of the pulse-like waves, for example by administering local anesthetics similar to the case of classic neural therapy.

The invention makes use of the fact that, given illness of an internal organ, on over-sensitivity and painfulness (hyperaesthesia and hyperalgesia) of certain skin zones occurs as a consequence of the spinal column segment-dependent supply of nerve signals to the internal organs. The reason for this is that the afferent back roots of the spinal nerves carry not only afferent, autonomic nerve fibers from the respectively appertaining organ zones but also carry them from skin segments (dermatoma). The ganglion critical for the respective malady can thus be identified on the basis of the over-sensitive and painful skin zones, which are also referred to as Head's zones, occurring in conjunction with an illness to be treated, and can be charged with the pulse-like wave. There is also the possibility of charging one or more Head's zones themselves as the neurally sensitive region or regions with the pulse-like wave in order to influence the appertaining organ or the appertaining organs for a therapeutic and/or diagnostic purposes.

In order to limit the action of the pulse-like wave only to the respective, neurally sensitive region and in order to ensure that the dose of energy supplied to the patient is not unnecessarily high even when more deeply seated neurally sensitive regions are to be reached, in a preferred modification of the invention the pulse-like wave is focused.

As in the case of manual therapy, a modification of the neural transmitters as well as of the biogenous amines occurs not only locally but in the entire organism after the treatment of a patient with the inventive apparatus or the inventive method. The corresponding investigations can be implemented according to the mood described by W. Kloepfer & Weth, G. et. al., "Atlas Therapy and Neurotransmitters in Patients Affected by Multiple Sclerosis", Manuelle Medizin, Vol. 27, No. 4, page 82, August 1989, Springer Verlag.

It has proven especially successful to conduct a mechanical wave onto the neurally sensitive region as a pulse-like wave, this being preferably generated with an acoustic pressure pulse source.

In this context, in a further embodiment of the invention the body surface of the patient is charged impact-like with a solid member on the basis of the pressure pulse source for generating the mechanical wave. A suitable apparatus can be constructed in a handy and simple way. As disclosed in U.S. Pat. No. 3,396,721 and by U.S. Pat. No. 4,265,228 such a suitable pressure pulse source contains, for example, a ram that can be electromagnetically driven impact-like as a solid member, the mechanical wave being generated by the impact thereof onto the body surface. The charging of the body surface with the ram can ensue directly or upon the interposition of an acoustic coupling agent. Alternatively the body surface of the patient is charged with a projectile emitted by the pressure pulse source for generating the mechanical wave. Suitable as projectiles, for example, are hollow balls of plastic, balls of expanded cellular material, cork balls, etc. It is self-evident that the energy of the projectile is so low that the patient is not wounded in anyway whatsoever.

The kinetic energy of the solid member preferably amounts to at least 5 millijoules. The velocity of the solid member should amount to at least 3 m/s since mechanical waves whose duration amounts to at most 100 ms are then introduced into the body of the patient. The mass of the solid member should amount to at least 1 g since the velocity of the solid member required for generating said kinetic energy is then kept within limits.

According to a further embodiment of the invention, the body surface of the patient, as disclosed by U.S. Pat. No. 3,861,383 is charged pulse-like with a fluid by the pressure pulse source for generating the mechanical wave. The pulse-like charging with the fluid corresponds in effect to charging the body surface with a projectile. Expediently, the pressure pulse source then contains a fluid volume in communication with the ambient atmosphere via an opening and that can be compressed impact-like, whereby the pressure pulse source emits the fluid charging the body surface of the patient through the opening when the fluid volume is suddenly compressed. A gas as well as a liquid can be employed as fluid.

According to a preferred embodiment, the mechanical wave is generated with an electromagnetic pressure pulse source, preferably in the form of an acoustic shock wave, i.e., a positive acoustic pressure pulse having an extremely steep leading edge. The employment of an electromagnetic pressure pulse source disclosed by European Application 0 301 360 is especially advantageous because such pressure pulse sources enable an extremely sensitive and well-reproducible setting of the acoustic properties of the generated pressure pulses. Other pressure pulse sources can also be employed, and capable of generating shock waves for example, piezoelectric, electrohydraulic and magnetostrictive pulse sources.

The amplitude of the mechanical wave or the pressure pulse is large (>factor 3) in terms of amount compared to the amplitude of potential delay events. Even though positive mechanical waves or pressure pulses (over-pressure) are preferably provided, it is also fundamentally possible to apply negative pressure pulses (under-pressure) insofar as it is assured that injury to the respective neurally sensitive region due to cavitation is precluded. Injury to the respective neurally sensitive region due to thermal influences is practically impossible since mechanical waves or, respectively, acoustic pressure pulses of said type are not accompanied by any noteworthy thermal phenomena and are merely applied singly.

According to a further version of the invention, an electromagnetic wave is conducted onto the neurally sensitive region. Particularly when the electromagnetic wave is focused, more deeply seated neurally sensitive regions can also be treated here, whereby the pulse-like electromagnetic wave can also be reproduced well with respect to its energy content as well as the temporal curve of its amplitude. A risk of, in particular, thermal injury to the respective neurally sensitive region is likewise not established since the electromagnetic waves, like the mechanical waves, are singly applied.

According to one embodiment of the invention, there is also the possibility of conducting an electrical pulse, into the neurally sensitive region as a pulse-like wave. Such an electrical pulse can be produced, for example, by an electrical discharge, such as a capacitor discharge. This is advantageous particularly when the pulse-like wave is to be generated with a device implantable into the patient. Such an implantable device can be constructed similar to an implantable defibrillator or heart pacemaker, whereby the electrical pulse can be supplied to the respective neurally sensitive region via a catheter-like electrode. By contrast to a defibrillator or heart pacemaker, or a means for treating pain disclosed by U.S. Pat. No. 5,119,832 however, a sequence of electrical pulses is not output nor is an electrical pulse output given the occurrence or, respectively, failure of a physiological event. On the contrary, only individual pulses are applied in the above-described way, these being capable of being triggered by the attending physician or by the patient himself, for example with wireless remote control.

Even when applying electromagnetic waves or electrical pulses, the application is usually limited to a region that differs from the painful region or the region to be influenced.

DESCRIPTION OF THE DRAWINGS

Exemplary embodiments of the invention are shown in the attached drawings.

DESCRIPTION OF THE PREFERRED EMBODIMENTS

Figure 1:
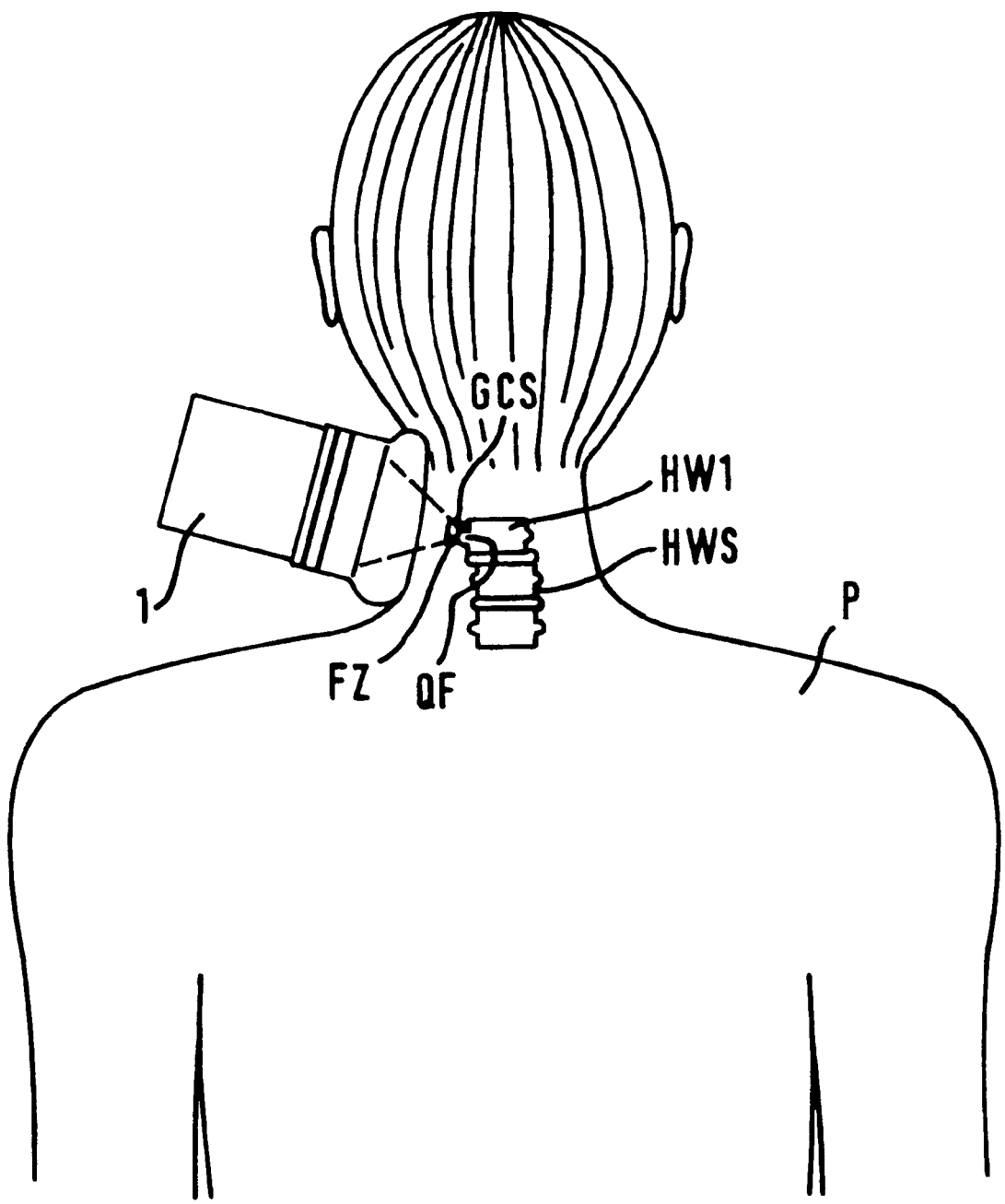
FIG. 1 illustrates the treatment of a patient with an acoustic shock wave source constructed, operating and applied in accordance with the principles of the present invention.

FIG. 1 shows a patient referenced P whose is suffering pain and stress in the region of his spinal column.

The cervical spinal column HWS of the patient P is schematically indicated in FIG. 1. It may thereby be seen from FIG. 1 that the first cervical vertebra HW1 comprises a dislocation, namely toward the left (out of view of the observer).

For treatment of this complaint with the inventive method or apparatus—only the pressure pulse source generally referenced 1 is shown in FIG. 1—a pulse-like mechanical wave, namely an acoustic pressure pulse in the form of a shock wave, is introduced into the patient P with the pressure pulse source 1. The acoustic pressure pulse source 1 is thereby acoustically applied from the left to the neck of the patient with a flexible coupling membrane, namely such that the focus zone FZ of the shock wave—the edge ways of the shock wave are indicated with broken lines in FIG. 1—lies in the region of the left transverse process UF of the dislocated, first cervical vertebra HW1. When a shock wave is then triggered, this strikes the ganglion cervicale superior GCS, which is schematically indicated in FIG. 1, lying in the region of the transverse process QF of the affected cervical vertebra HW1.

The ganglion cervicale superior is restimulated due to the incidence of the shock wave, the result being the readjustment of the nerve pathways dependent on the ganglion cervicale superior. As a result, the sensation of pain is at least alleviated and the stresses subside. The success of the treatment occurs practically immediately after the application of the shock wave.

A one-time treatment is not adequate for achieving a longer-lasting treatment success; on the contrary, a multiple, for example three-fold treatment is possible, whereby the individual treatments should lie at roughly the spacing of a week.

As a rule, it will suffice to apply a single shock wave per treatment. Fundamentally, however, it is also possible to apply sequences of shock waves.

Suitable pressure pulse sources are disclosed, for example, in U.S. Pat. No. 4,697,588, U.S. Pat. No. 4,764,505 and in European Application 0 301 360.

The structure of the pressure pulse source 1 shall be set forth in greater detail below with reference to FIG. 2 as an example.

Figure 2:
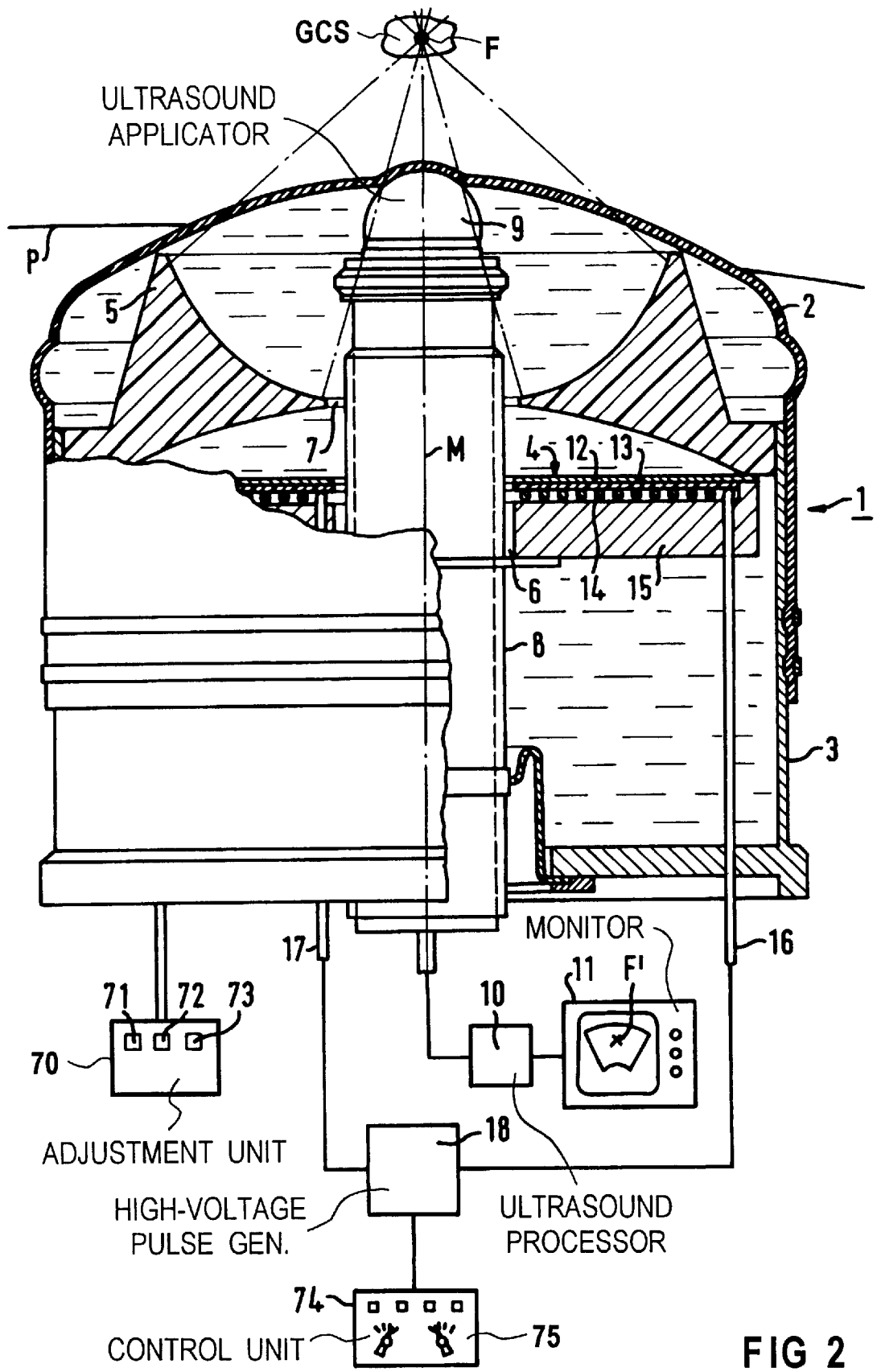
FIG. 2 shows the pressure pulse source of FIG. 1 in a longitudinal section.

The pressure pulse source 1 of FIG. 2 has an approximately pot-shaped housing 3, a shock wave generator generally referenced 4 being provided in the region of one end thereof. At its open end, the housing 3 of the pressure pulse source 1, which, moreover, is fashioned essentially dynamically balanced relative to the center axis M, is closed with the flexible coupling membrane 3. With the latter, the pressure pulse source 1 is pressed against the body of the patient P in the way shown in FIG. 1 for acoustic coupling. The housing 3 is filled with water that is provided as acoustic propagation medium for the shock waves emanating from the shock wave generator 4.

The shock wave generator 4 is an electromagnetic shock wave generator. The shock wave generator 4 is preceded by an acoustic positive lens 5 that serves the purpose of focusing the planar shock waves emanating from the shock wave generator, those shock waves, as shown with broken fines in FIGS. 1 and 2, then converging on the focus zone F lying on the center axis M. The shock wave generator 4 and the positive lens 5 are provided with central openings 6 and 7 aligned with one another and through which a tube 8 extends. An ultrasound applicator 9 is arranged in this tube 8 and allows ultrasound B-images of a slice of the body of the patient containing the center axis M and the focus zone F of the shock waves to be produced with a schematically indicated ultrasound processor 10.

Using the ultrasound locating means formed by the ultrasound applicator 9 and the ultrasound processor 10 and/or using a known x-ray locating means that is not shown, it is possible in a known way to align the pressure pulse source 1 relative to the body of the patient such that a region to be charged with the shock waves, for example the transverse process QF or the ganglion cervicale superior GCS is located in the focus zone F of the shock waves, as shown in FIG. 1. This occurs with the assistance of a mark F' identifying the position of the focus zone F that is mixed into the ultrasound B image displayed on a monitor 11 in a known way.

In order to be able to align the pressure pulse source 1 relative to the patient in the described way, it is spatially adjustable with a known adjustment unit 70 having operating elements 71, 72 and 73. The pressure pulse source 1 thus can be aligned relative to the stationary body of the patient P so that the focus zone F of the shock waves lies within the neurally sensitive region GCS, as shown in FIG. 1. This occurs with the assistance of the mark F' identifying the position of the focus F. The "edge rays" of the shock waves are indicated with broken lines in the figures.

Other adjustment possibilities, are possible in order to relatively position the neurally sensitive region GCS and the pressure pulse source 1 (more specifically the focus F thereof). These adjustment possibilities include adjusting only the patient P, or adjusting the patient P as well as the pressure pulse source 1.

The ultrasound applicator 9, moreover, is longitudinally displaceable in the direction of the center axis M in the tube 8 and is also arranged so it can be swivelled around the center axis M in order, dependent on the given situation of the respective treatment case, to be able to generate an informative ultrasound B-image that is disturbed as little as possible and in order to be able to bring the dome-shaped sound exit window of the ultrasound applicator 9 into engagement with that side of the coupling membrane 2 adjoining the acoustic propagation medium in the way required for a good image quality. The other side thereof presses against the body surface of the patient. The position of the mark F' is thereby matched in a known way to the respective position of the ultrasound applicator 9. The adjustment units required for the described adjustment of the ultrasound applicator 9 can be realized without further difficulty by a person skilled in the art and are therefore not shown.

The shock wave generator 4 has a planar membrane 12 containing an electrically conductive material, for example copper or aluminum, the one side of said planar membrane 12 adjoining the water located in the housing 3. The other side of the membrane 12 lies against a helically wound flat coil 14 that, for example, is applied on a coil carrier 15 by gluing. An insulating foil 13 is disposed between the membrane 12 and the flat coil 14. The flat coil 14 is in communication via terminals 16 and 17 with a high-voltage pulse generator 18 with which the flat coil 14 can be charged with high-amperage high-voltage pulses (kV and kA range). The high-voltage pulse generator 18 is fashioned such that the intensity of the shock waves and the repetition rate of the shock waves are variable. To this end, a control unit 74 having a control panel 75 is provided, this being connected to the high-voltage pulse generator 18 and allowing the intensity and reception rate to be set.

When the flat coil 14 is charged with a high-voltage pulse, eddy currents are induced into the membrane 12, these eddy currents flowing in a direction opposite the current flowing through the flat coil 14. This results in the magnetic field belonging to the eddy currents and the magnetic field belonging to the current flowing through the flat coil 14 being oppositely directed. The membrane 12 thus suddenly moves away from the flat coil 14. As a result, a shock wave is formed in the water located in the housing 3, this shock wave being focused with the acoustic positive lens 5. The pulse duration of the generated shock wave lies in the $\mu$s range, i.e. is dearly below 100 ms. The energy of the generated shock wave can lie on the order of magnitude of up to 120 millijoules, whereby the energy density in the focus can amount to up to approximately 0.6 millijoules/$mm^2$. The peak pressure in the focus can amount to up to 700 bar.

Although it is especially advantageous to employ an electromagnetic pressure pulse source of the described type, since these can be well-regulated, other pressure pulse sources, for example piezoelectric (U.S. Pat. No. 4,526,168), magnetostrictive, electrohydraulic (German Published Application 23 51 247) and other shock wave sources can be employed within the framework of the invention. The pressure pulse sources employed within the framework of the invention also need not necessarily be shock wave sources.

Acoustic pressure pulse sources that generate acoustic pressure pulses that cannot be classified as shock waves can also be employed. As an example, pressure pulse sources that generate acoustic under-pressure pulses may be employed.

Figure 3:
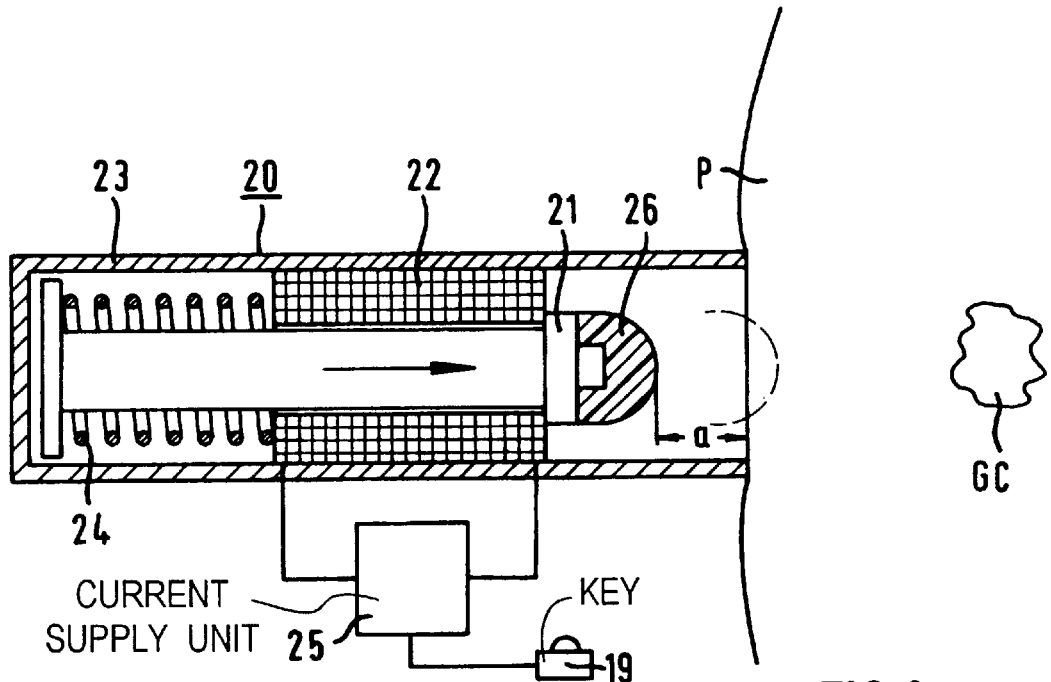
FIG. 3 illustrates the treatment of a patient with a further embodiment of an inventive pressure pulse source constructed differently from FIGS. 1 and 2.

A further embodiment of the invention is shown in FIG. 3. The treatment ensues here with a pressure pulse source 20 that, for generating a pressure pulse, charges the body surface of the patient P with a solid member, namely a ram 21, impact-like. An annular electromagnet 22 in whose bore the ram 21 is accepted longitudinally displaceable is provided for driving the ram. The ram 21 and the electromagnet 22 are accepted in a tubular housing 23 closed at one end by a base. At the other end, which is the application end, the housing 23 is open. A restoring spring 24 is provided in order to bring the ram 21 into a defined initial position. The initial position of the ram 21 is selected such that it has a defined spacing A from the body surface of the patient P when the application end of the housing 23 is put in place onto the body surface of the patient P. When the electromagnet 22 is charged with a current pulse from a current supply unit 25 in response to actuation of the key 19, the ram 21 is suddenly driven in the direction onto the body surface of the patient P, this being indicated in FIG. 3 with a corresponding arrow. The ram 21, which is provided with a rubber cap 26 at its end facing toward the body surface of the patient P, impacts the body surface of the patient P, as indicated in broken lines in FIG. 3. As a result, an acoustic pressure pulse is introduced into the body of the patient and impinges the ganglion coeliacum that is referenced GC and schematically indicated in FIG. 3. As a result of the restimulation of the ganglion coeliacum GC effected in this way, pain triggered by aliments in the upper abdomen can be eliminated. For example, it is thus possible that the pains caused by a pancreatitis can be eliminated, these being nearly always resistant to therapy and having to be treated by high doses of morphine preparations.

After the incidence of the ram 21 on the body surface of the patient, the ram 21 is returned by the restoring spring 24 into its initial position shown in FIG. 3.

In order to be able to apply the pressure pulse source 20 exactly in be position required on the body surface of the patient P, the application end of the housing 23 can be made transparent or provided with cut-outs, neither of which is shown.

The current supply unit 25 can, for example, be constructed such that it contains a number of capacitors that are charged by a current source in parallel and, upon actuation of the key 19, are connected in series and are connected to the terminals of the electromagnet 22. In this way, economic capacitors having low electric strengths and a economic low-voltage current source can be employed.

Preferably, the mass of the ram 21 amounts to at least 1 g. The velocity of the ram 21 upon incidence onto the body surface is at least equal to 3 m/s. The kinetic energy of the ram 21 upon incidence onto the body surface of the patient P is at least equal to 5 millijoules. It is then assured that the duration of the pressure pulse introduced into the body of the patient P does not exceed 100 ms, this being the prerequisite for a good therapy result.

Figure 4:
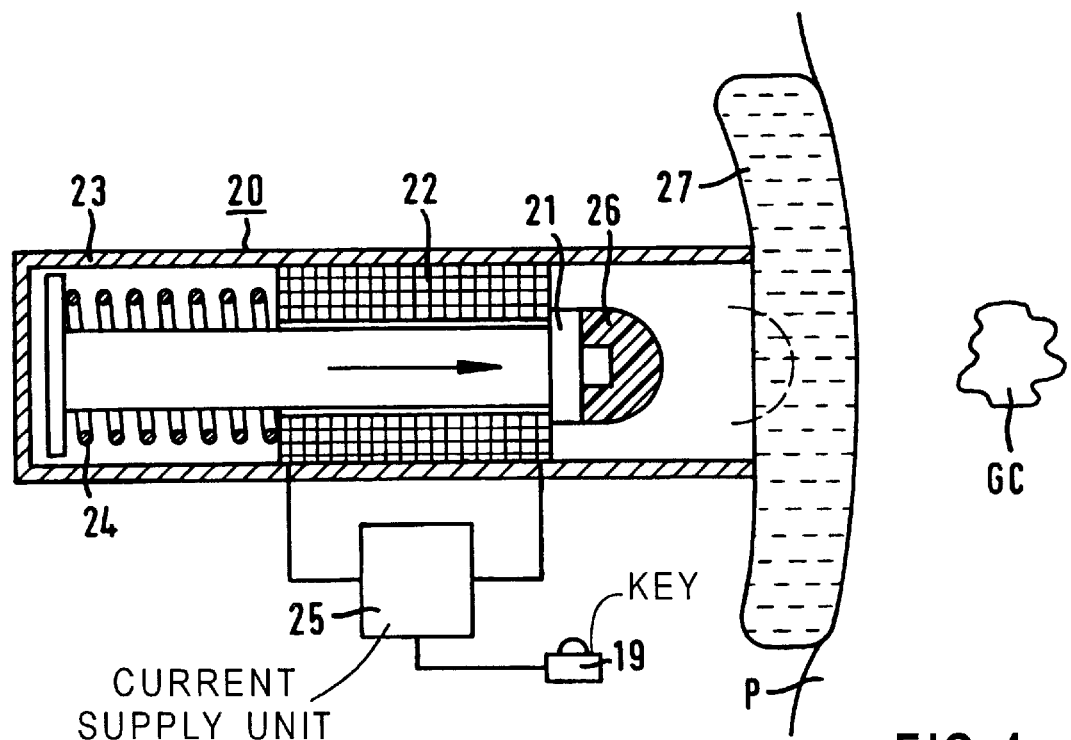
FIG. 4 illustrates a modification of the pressure pulse source of FIG. 3.

In the case of the apparatus or method illustrated in FIG. 3, the ram 21 directly strikes the body surface of the patient P with its rubber cap 26. In order to create defined impact conditions for the ram 21, however, there is also the possibility of providing a coupling member 27 according to FIG. 4 that is put in place onto the body surface of the patient P in the region of the application zone. The coupling member 27, for example, can be a disk composed of a hydrogel. An improved reproducibility of the pressure pulses introduced into the body of the patient P is achieved as a result of this measure.

Figure 5:
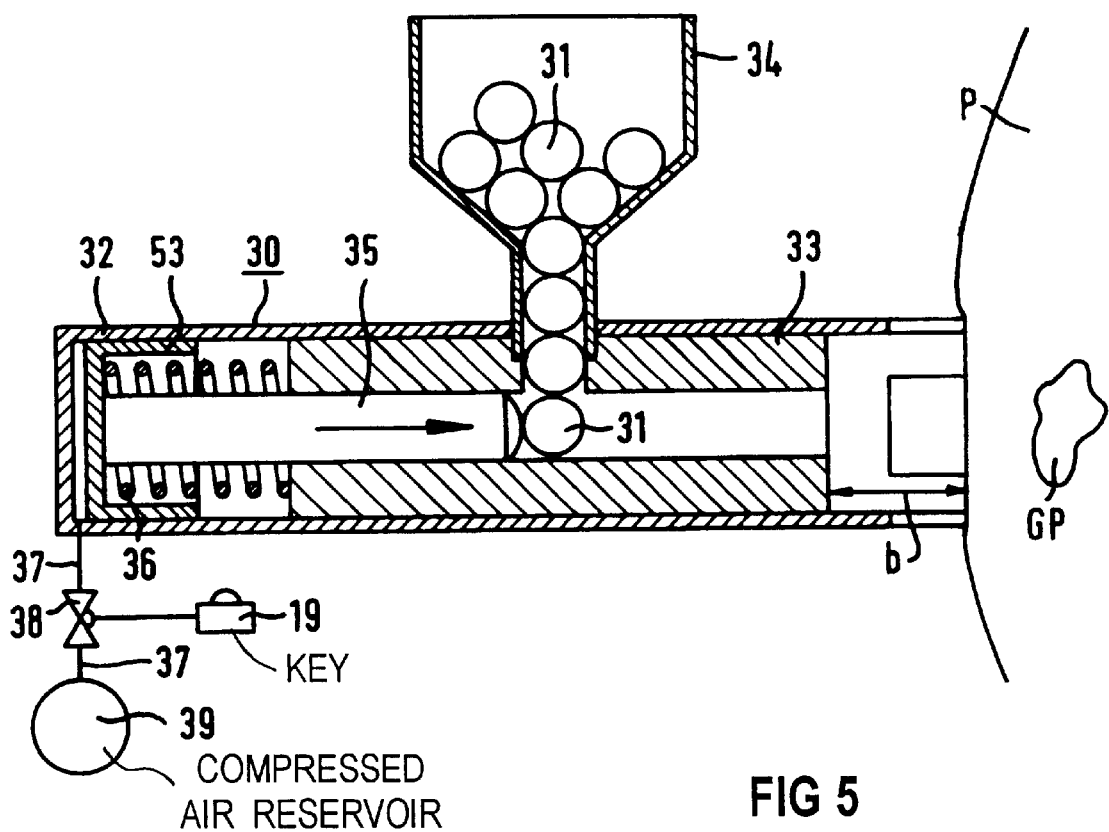
FIGS. 5 through 7 respectively illustrate further embodiments of an inventive pressure pulse source in illustrations analogous to FIG. 3.

FIG. 5 shows another version of apparatus or method of the invention. Here, the pressure pulse is likewise generated by charging the body surface of the patient P with a solid member. This solid member, however, is not a ram but is instead a spherical projectile 31 that can be formed, for example, of cork, expanded cellular material, cotton wadding or the like. However, a hollow ball, for example of plastic, can also be employed as projectile 31. The velocity, mass and energy of the projectile 31, are as set forth above with respect to the ram 21, i.e. pressure pulses whose duration lies below 100 ms are introduced into the body given the apparatus or method of FIG. 5.

In the case of the apparatus or method illustrated in FIG. 5, the pressure pulse introduced into the body of the patient P strikes the ganglion pelvinum that is schematically indicated in FIG. 5 and referenced GP. As a consequence of the restimulation of the ganglion pelvinum effected by the pressure pulse charging, pains in the region of the lumbar spinal column and in the sacrale region can be therapeutically treated.

The pressure pulse source 30 also has a tubular housing 32 that is open at its application end. A barrel 33 whose diameter corresponds to the diameter of the projectile 31 is inserted into the housing 32. A transverse bore that also extends through the housing 32 and serves the purpose of supplying projectiles 31 accepted in a container 34 discharges into the bore of the barrel 33.

A piston 35 that is longitudinally displaceable in the barrel 33 is provided in order to be able to drive a projectile 31 located in the barrel 33 impact-like. In its initial position, into which it is brought with a restoring spring 36, it just clears the transverse bore, so that a projectile 31 can proceed into the barrel 33 in the way shown in FIG. 5.

In order to be able to "shoot" the projectile 31 located in the barrel 33 onto the body surface of the patient P for producing a pressure pulse, the space located between the floor of the housing 32 and that end of the barrel 33 adjacent thereto can be connected to a compresses air reservoir 39 via a line 37 into which a valve 38 controlled via the key 19 is connected. The valve 38 is fashioned such that it normally produces a connection of the interior of the housing 32 to the ambient atmosphere and only briefly produces a connection to the compresses air reservoir 39 when the key 19 is actuated. A drive piston 33 that is accepted longitudinally displaceably in the housing 32 and is rigidly connected to the piston 35 suddenly drives the piston 35 in the direction onto the body surface of the patient P, and thus the projectile 31 located in the barrel 33 charges the body surface of the patient P.

Thereafter, the restoring spring 36 brings the piston 35 back into its initial position shown in FIG. 5 wherein a new projectile 31 can proceed through the transverse bore into the barrel 33. In the region of its application end, moreover, the housing 32 is provided with cut-outs through which the projectile 31 can fall out of the housing 32 after charging the body surface. The cut-outs simultaneously serve as a viewing window. Given a pressure pulse source 30 applied to the body surface of the patient, the end of the barrel 33 comprises the defined spacing B from the body surface.

Figure 6:
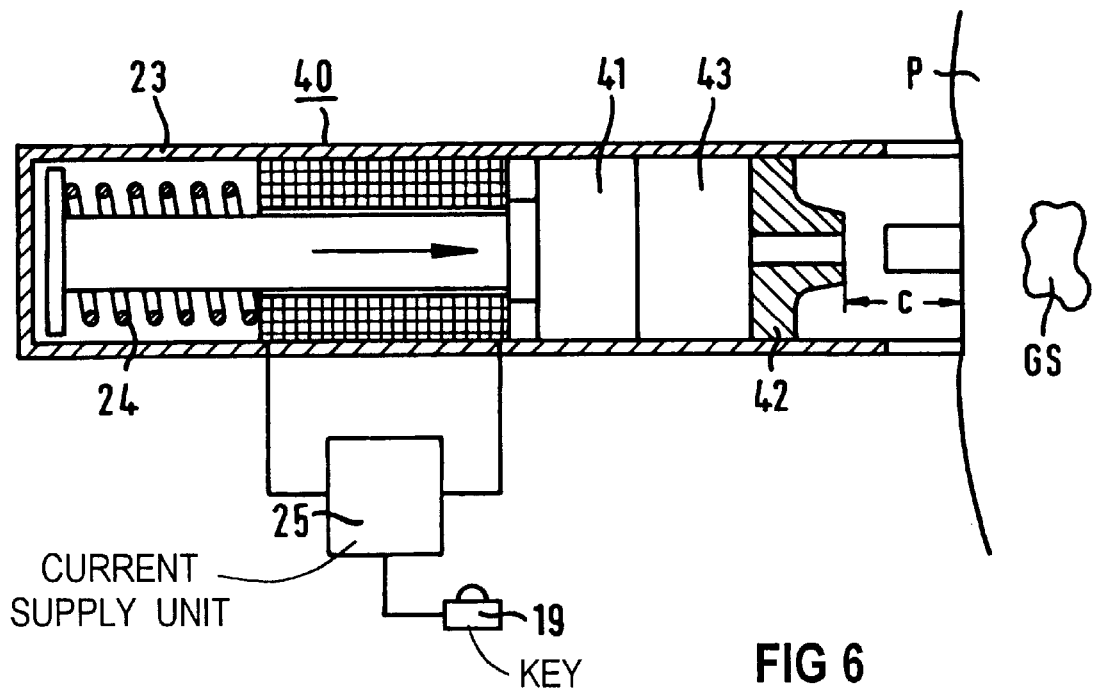

The apparatus or method illustrated in FIG. 6 is suitable, for example, for the treatment of lumbago since the ganglion sacrale that is indicated in FIG. 6 and referenced GS is charged with a pressure pulse here. A practically immediate freedom from the complaint can be achieved by the restimulation of the ganglion sacrale as a consequence of the pressure pulse that has been introduced.

The pressure pulse source 40 employed in the apparatus or method of FIG. 6 is similar to the pressure pulse source 20 of FIG. 3, with the difference that instead of a ram 21 the body surface of the patient P is charged by a piston 41 that is electromagnetically driven, the piston 41 compressing an air volume 43 located within the housing 23, so that a pulse-like air stream emerges through a nozzle 42 placed into the end of the housing 23 adjacent to the body surface of the patient. The area of the piston 41, the size of the air volume 43 and the cross section of the nozzle 42 and the spacing C thereof from the body surface are matched such that a pulse duration that does not exceed 100 ms is produced under given drive conditions for the pressure pulse introduced into the body of the patient P.

The application end of the housing 23, that is placed onto the body surface of the patient for treatment in the way shown in FIG. 6, is provided with cut-outs, so that the space bounded by the housing 23 and the body surface of the patient P when the pressure pulse source 40 is applied is in communication with the ambient atmosphere. Moreover, the body surface of the patient P is visible through the cut-outs.

Figure 7:
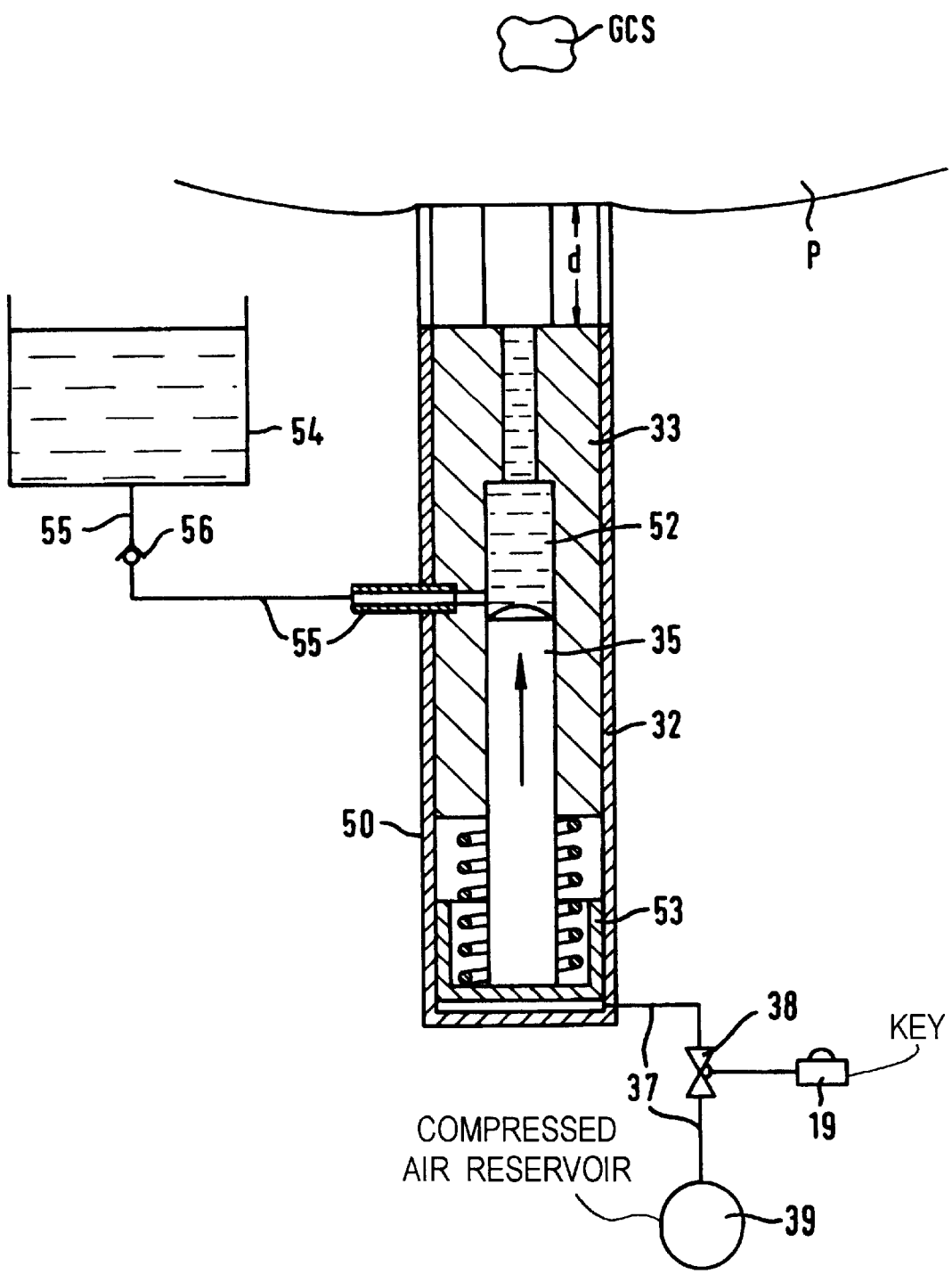

In the case of the apparatus or method illustrated in FIG. 7, as in the case of FIG. 1, a pressure pulse is introduced into the ganglion cervicale superiors . This however, is not for treating maladies in the spinal column region but instead is for the treatment of autonomic nervous system disorders, for example cardiac rhythm disorders as can occur, for example, in conjunction with hyperkinetic heart syndrome.

The pressure pulse source 50 employed in the case of FIG. 7 is similar to the pressure pulse source 30 of FIG. 5, whereby, however, the body surface of the patient P is not charged with projectiles 31 but with pulse-like liquid surges. For example, water can be employed as the liquid. The water is accepted in a container 54 that is connected via a line 55 and the transverse bore penetrating the housing 32 and the barrel 33 with that part of the barrel 33 located in front of the piston 35, so that this part of the barrel 33 receives a liquid volume 52. It is self-evident that the pressure pulse source 50, as likewise shown in FIG. 7, must be operated in such an attitude that the water situated in the barrel 33 cannot escape. This measure can be omitted when a viscous liquid is employed instead of water, which will not run from the barrel even when the barrel 33 is directed downwardly. In order to avoid a return of water from the liquid volume into the container 54, a one way valve 56 can be connected into the line 55, as shown in FIG. 7.

Similar to the case of the pressure pulse 40 of FIG. 6, the area of the piston 35, the volume of the barrel 33 filled with liquid, the cross section of the barrel 33 and the distance D of the end of the barrel 33 from the body surface of the patient P are selected such that the pressure pulses introduced into the patient P due to the pulse-like surface of the liquid sprayed from the barrel 33 onto the body surface of the patient P have a duration that does not exceed 100 ms.

It is self-evident that the measures undertaken in conjunction with the pressure pulse sources 20, 30, 40 and 50 for driving the ram or the pistons 35 and 41 are to be understood only as examples. Other measures can be undertaken insofar as it is merely assured that the duration of the generated pressure pulses does not exceed 100 ms.

In the case of all exemplary embodiments set forth above, the pressure pulses introduced into the body of the patient should have an energy of at least 5 millijoules.

Figure 8:
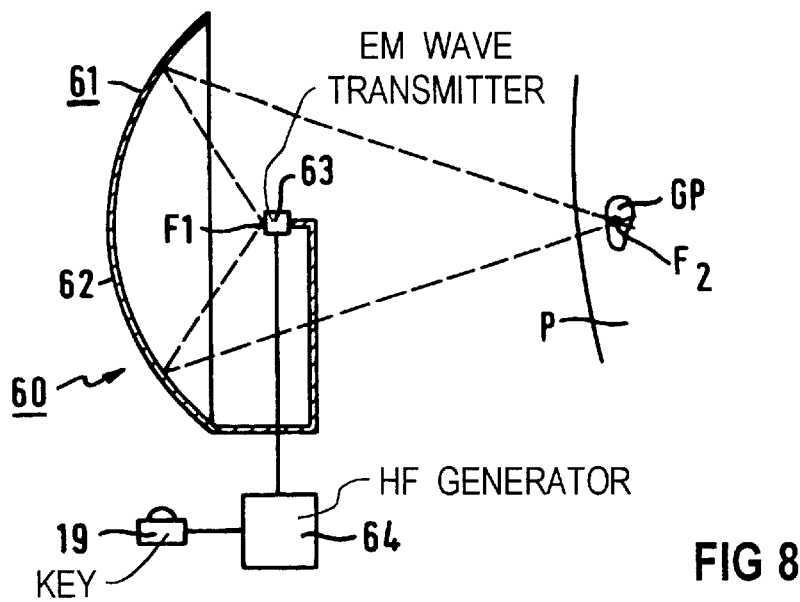
FIG. 8 illustrates the treatment of a patient with a source of pulse-like electromagnetic waves in accordance with the principles of the present invention.

FIG. 8 shows an inventive apparatus or method that allows the same therapeutic effects to be produced as in the case of the above-described exemplary embodiments. However, no acoustic pressure pulses are introduced into the body of the patient using the apparatus and method of FIG. 8. Instead the ganglion to be re-stimulated is charged with a pulse-like electromagnetic wave. The ganglion, for example, can be the ganglion cervicale superior, the ganglion coeliacum, the ganglion pelvinum or the ganglion sacrale.

The pulse-like electromagnetic wave is introduced into the ganglion in the case of the apparatus and method illustrated in FIG. 8.

A transmitter 60 means for the pulse-like electromagnetic wave generally has a transmission antenna 61 that contains a concave reflector 62 that is formed as a section of an ellipsoid. A transmitter 63 for emitting pulse-like electromagnetic waves is arranged in the focal point $F_1$ of the ellipsoid which is located closer to the concave reflector 62. These electromagnetic waves are focused onto the second focal point $F_2$ of the ellipsoid by the concave reflector 62. The transmitter 63 is supplied by a high-frequency generator 64. In the treatment, the arrangement of the patient P and of the transmission means 60 relative to one another is selected such that the ganglion pelvinum GP is located at least approximately in the second focal point $F_2$, so that it is charged by the pulse-like electromagnetic waves.

It can be expedient to ensure a good matching between the transmitter 60 and the body of the patient P by using a suitable dielectric material deviating from air, for example, a ceramic compound.

The arrangement shown in FIG. 8 is presented only as an example. Focused pulse-like electromagnetic waves need not necessarily be employed. Dependent on whether the pulse-like electromagnetic waves are focused or unfocused, moreover, a number of transmission means can be employed, these being aligned such that the pulse-like electromagnetic waves they respectively transmit are superimposed in the region of the respective ganglion, for example the ganglion pelvinum.

Figure 9:
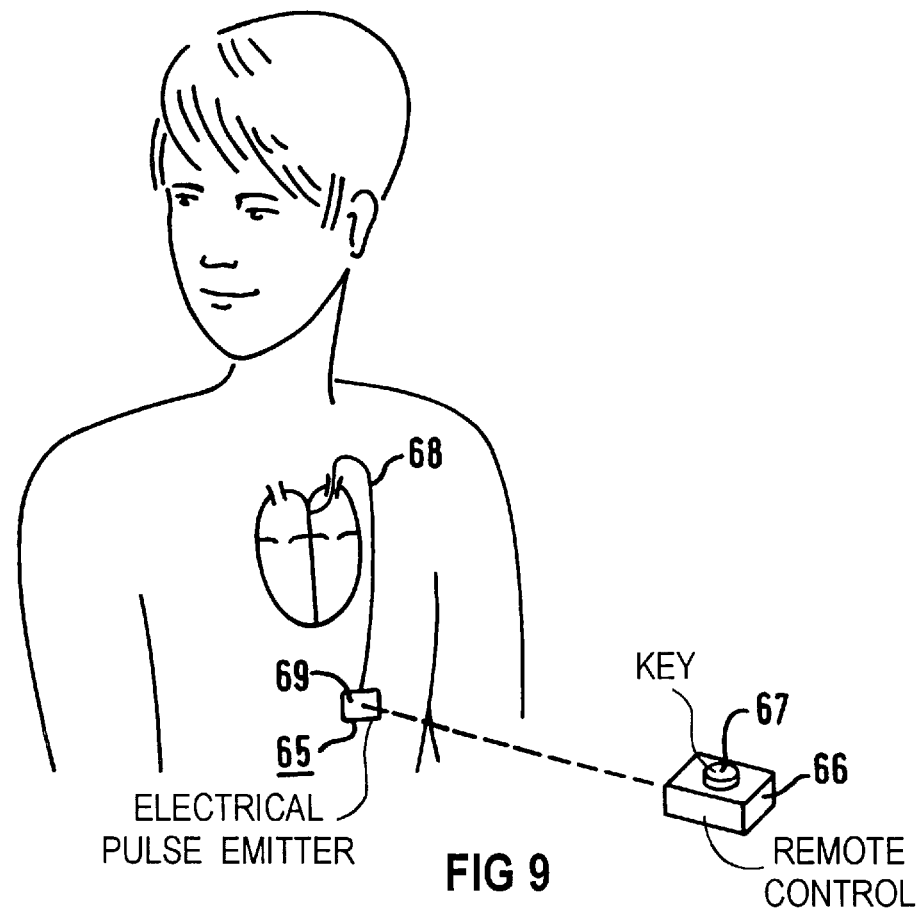
FIG. 9 illustrates the treatment of a patient with electrical pulses in accordance with the principles of the present invention.

FIG. 9 shows an inventive apparatus and method that allows the same or similar therapeutic effects to be produced as in the case of the above-described exemplary embodiments. However, no acoustic pressure pulse or no pulse-like electromagnetic wave is introduced into the body of the patient in the case of the apparatus and method of FIG. 9. Instead, the respective ganglion to be restimulated is charged with an electrical pulse. As schematically indicated in FIG. 9, the electrical pulse is thereby preferably generated with an apparatus implantable into the body of the patient.

The apparatus 65 is constructed similar to known, implantable defibrillators or heart pacemakers, with the difference that the electrical pulses are not automatically generated in response to the occurrence of a specific event (heart flutter) or in response to the failure of a specific event (natural heart beat given synchronous heart pacemakers) or in the form of periodically repeating pulses (given asynchronous heart pacemakers). The output of an electrical pulse, on the contrary, only ensues when an operating element of the apparatus 65 is actuated.

The operating element in the case of the apparatus 65 is a wireless remote control 66 having a key 67 in response to whose actuation of the apparatus 65 emits an electrical pulse.

The electrical pulse is supplied to the respective, neurally sensitive region via active electrode 68 preferably, but not necessarily transvenously disposed. The indifferent, i.e. passive electrode is preferably formed by the electrically conductive housing 69 of the apparatus 65 implanted, for example, under the chest muscles or into the peritoneum.

A disorder in the activity of the heart muscle, namely a heart rhythm disorder, for example, tachycardia, is treated in the case of the apparatus and method shown in FIG. 9. The electrical pulse generated with the apparatus 65 is introduced into the heart in the atrium or ventricle region with the electrode 68 for this purpose.

The restimulation of the conduction system effects an elimination of the disorder, so that even patients previously dependent on antiarhythmica can manage without mediation.

The heart can also be influenced by charging autonomic (vagus and sympathetic), centrally regulating, neurally sensitive regions (for example, ganglion coeliacum) with pulse-like waves.

The inventive application of electrical pulses is not limited to the treatment of heart rhythm disorders. Disorders of the autonomic nervous system and painful conditions of all types can be treated as well, whereby the critical ganglion is then to be charged with the electrical pulse. An implantable device thereby need not necessarily be employed.

The above-described apparatus for the implementation of the inventive method are to be understood only as examples. Differently fashioned devices can likewise be employed.

Likewise, the neurally sensitive regions cited as the points of application for the treatment are only to be understood as examples. This is also true of the maladies cited as being capable of being treated.

Although modifications and changes may be suggested by those skilled in the art, it is the intention of the inventors to embody within the patent warranted hereon all changes and modifications as reasonably and properly come within the scope of their contribution to the art.

We claim as our Invention:

1. A method for medical therapy comprising the steps of:

selecting a neurally sensitive body region of a subject, said neurally sensitive body region comprising a nerve center; and producing at least one focused pressure pulse using an electromagnetic pressure pulse source and non-destructively charging said neurally sensitive body region with said at least one focused pressure pulse for effecting a therapeutical effect of the group consisting of at least alleviating pain in a region within the body of said subject associated by transmission of stimuli with said neurally sensitive body region and influencing a part of the autonomic nervous system of said subject associated by transmission of stimuli with said neurally sensitive body region.

2. A method as claimed in claim 1 wherein the step of charging said neurally sensitive body region with at least one pressure pulse wave comprises charging said neurally sensitive body region with at least one pressure pulse having a duration not significantly exceeding 100 ms.

3. A method as claimed in claim 1 wherein the step of charging said neurally sensitive body region with a pressure pulse comprises charging said neurally sensitive body region with an acoustic shock wave produced by said electromagnetic pressure pulse source.

4. A method as claimed in claim 1 comprising the additional step of identifying a site of said pathological condition in the body of said subject, and wherein the step of selecting said body region comprises selecting a neurally sensitive region of said body remote from said site.

5. A method as claimed in claim 1 wherein the step of selecting said neurally sensitive body region comprises selecting a neurally sensitive region close to a transverse process of the first cervical vertebra of said subject.

6. A method as claimed in claim 5 wherein the step of selecting a neurally sensitive body region close to a transverse process of the first cervical vertebra comprises selecting the ganglion cervical superior.

7. A method as claimed in claim 1 wherein the step of selecting a neurally sensitive body region comprises selecting a ganglion as said neurally sensitive body region.

8. A method as claimed in claim 7 wherein the step of selecting a ganglion comprises selecting a ganglion from the group consisting of the ganglion coelicum, ganglion cervical superior, ganglion pelvinum and ganglion sacrale.

9. A method as claimed in claim 1 wherein the step of charging said neurally sensitive body region with at least one pressure pulse comprises charging said neurally sensitive body region with a plurality of pressure pulses, and comprising the additional step of maintaining a minimum chronological spacing between successive ones of said pressure pulses of several minutes.

* * * * *